United States Patent [19]

Kawamata et al.

[11] Patent Number: 4,769,183
[45] Date of Patent: Sep. 6, 1988

[54] STABILIZATION OF AZULENE DERIVATIVES

[75] Inventors: Masanobu Kawamata; Koichi Ushimaru, both of Kyoto; Hiroyuki Goshi, Shiga; Hideichi Miyasako, Moriyama, all of Japan

[73] Assignee: Nippon Shinyaku Co., Ltd., Japan

[21] Appl. No.: 473,453

[22] Filed: Mar. 9, 1983

[51] Int. Cl.$^4$ ............................................ C07C 143/22
[52] U.S. Cl. ................................................... 260/503
[58] Field of Search ................ 260/503, 505 R, 505 P

[56] References Cited

PUBLICATIONS

Weissberger, Separation & Purification, Part 1, vol. III, (1956), pp. 821–822, 831–833.
Perry, Perry's Chem. Eng. Handbook, 4th Ed., (1963), pp. 17–58.

Primary Examiner—Nicky Chan
Attorney, Agent, or Firm—Jacobs & Jacobs

[57] ABSTRACT

Sodium 1,4-dimethylisopropylazulene-3-sulfonate is stabilized by dissolving it in a suitable solvent and thereafter removing the solvent from the solution by spray-drying or lyophilization.

11 Claims, No Drawings

STABILIZATION OF AZULENE DERIVATIVES

The present invention relates to a method of stabilizing sodium 1,4-dimethylisopropylazulene-3-sulfonate (abbreviated hereinafter as GASN) which is a water soluble derivative of guaiazulene.

GASN exhibits anti-inflammatory and anti-ulcer activity and is widely used as a pharmaceutical in the form of tablets or granules. Though GASN is soluble in warm water, alcohol and acetic anhydride, it is sparingly soluble in cold water and is nearly insoluble in ether and benzene. Therefore, it is usually purified by recrystallizing from water.

Crystals obtained by recrystallization from water are needles or flakes.

GASN is an unstable compound even in its solid state and decomposes even at room temperatures. Thus it is not possible to store it for a long time even in composition forms such as tablets and granules.

Several attempts at stabilizing GASN against heat have been reported such as by adding weakly basic metal salts or alkali earth metal salts (cf. German Pat. No. 1,034,327) or, more recently, by adding an amino acid (cf. Japanese Patent Publication No. Sho-49-11219). There are, however, several disadvantages to those methods such as that addition of a stabilizer is necessary or the resulting effect is not always satisfactory.

The stabilization method according to the present invention comprises dissolving GASN in a suitable solvent and then rapidly removing the solvent by the method which is further described below.

More particularly, GASN is dissolved in water, lower aliphatic alcohols or an aqueous solution of such alcohols and then the solvent is removed therefrom by spray-drying or by lyophilization. Examples of suitable lower aliphatic alcohols are straight or branched chain alcohols with one to four carbon atoms and, among them, methyl alcohol or ethyl alcohol is preferred. When such alcohols are used as aqueous solutions thereof, there will be no particular restriction in concentration.

One of the most important aspects of the present invention is the method of evaporating the solvent. Both spray-drying and lyophilization which have not been applied as methods for stabilization are particularly suitable according to the present invention whereupon a solute which is stable against heat is obtained.

When the solvent is removed under ordinary pressure or by such an apparatus as a rotary evaporator in vacuo, the solution is concentrated and a part of the solute appears as crystals. But, there is no hope of obtaining stabilized solute by such methods. Removal or separation of the solvent by spray-drying or by lyophilization is required.

Powder X-ray diffraction of the GASN obtained by the present invention does not show particular peaks as compared with that of the crystalline form and it is clear that the product is in non-crystalline form. This is one of the most important features of GASN obtained by the present invention method.

The following non-limitative examples more particularly illustrate the present invention:

EXAMPLE 1

GASN (50 grams) is dissolved in 5 liters of water of 25° C. and subjected to a spray-drying using a mobile minor type spray drier (Niro Company) at a spray drying rate of 2 liters per one hour (temperature of supplied air is 100° C.) to give finely powdery GASN.

EXAMPLE 2

GASN (50 grams) is dissolved in 5 liters of water of 25° C., 4950 grams of lactose is subjected to flowing at the condition of air in-taking temperature of 70° C. using a fluidized bed grain manufacturing apparatus WSG-5 (Gratt-Okawara), and the above solution is sprayed at 100 ml/minute and dried to give a composition containing 1% GASN.

EXAMPLE 3

GASN (50 grams) is dissolved at room temperatures in 3.5 liters of 50% methanol and treated by the same way as in Example 2 ( air intaking temperature: 60° C.) to give a composition of GASN:lactose=1:99.

EXAMPLE 4

GASN (1 gram) is dissolved in 100 ml of water and subjected to lyophilization by a lyophilizer (DC-35, Yamato Co) using actone-dry ice as a freezing mixture.

GAS obtained in Examples 1 to 4 are allowed to stand at 40° C. after made into the samples as illustrated later and the residual GASN is measured by the formula $$\text{Amount of } GASN \text{ (mg)} = \frac{A}{20.25} \times 1000$$

by observing an extinction at 568 nm in a phosphate buffer of pH 7.0. The stability data after stored at 40° C. are given in Table 1.

Method of manufacturing samples are as follows.

Sample 1: One gram of GASN obtained in Example 1 is mixed with 99 grams of lactose to make 100 grams.

Sample 2: The composition obtained in Example 2 is used as it is.

Sample 3: The composition obtained in Example 3 is used as it is.

Sample 4: One gram of GASN obtained in Example 4 is mixed with 99 grams of lactose to make 100 grams.

Control: One gram of untreated GASN is mixed with 99 grams of lactose to make 100 grams.

Each sample is placed in Petri dishes and the upper part is tightly closed with polyethylene film.

TABLE 1

| | Residual Rate (in %) of GASN treated at 40° C. | | | | |
| --- | --- | --- | --- | --- | --- |
| Samples | Immediately after Manufg | 1 Week | 2 Weeks | 3 Weeks | 4 Weeks after |
| 1 | 100 | 97.9 | 91.4 | 80.3 | 68.6 |
| 2 | 100 | 98.9 | 97.1 | 94.1 | 92.6 |
| 3 | 100 | 97.8 | 95.3 | 93.4 | 90.4 |
| 4 | 100 | 98.1 | 79.6 | 54.1 | 28.7 |
| Control | 100 | 26.3 | 3.5 | 0 | 0 |

(Qualitative data immediately after manufacturing are set 100)

Table 1 shows that, as compared with the control, GASN obtained by the present invention method is considerably more stable.

In the above methods, addition of inert or active soluble additives to GASN solutions followed by similar treatment will not destroy the stability of GASN so far as the above procedure for rapid removal of the solvent is followed. It is incidentally found that the stability of GASN compositions to which insoluble additives are added is nearly the same as those of the compositions of Example 2 and 3.

We claim:

1. A method of stabilizing sodium 1,4-dimethylisopropylazulene-3-sulfonate in non-crystalline form which comprises dissolving sodium 1,4-dimethylisopropylazulene-3-sulfonate in a suitable solvent and removing the solvent from the solution by spray-drying or lyophilization.

2. A method according to claim 1 wherein the solvent is water, a lower aliphatic alcohol or an aqueous solution of a lower aliphatic alcohol.

3. A method according to claim 1 wherein the solvent is water.

4. A method according to claim 1 wherein the solvent is a lower aliphatic alcohol.

5. A method according to claim 4 wherein the lower aliphatic alcohol is a straight or branched chain alcohol of 1-4 carbon atoms.

6. A method according to claim 5 wherein the alcohol is methyl alcohol or ethyl alcohol.

7. A method according to claim 1 wherein the solvent is an aqueous solution of a lower aliphatic alochol.

8. A method according to claim 7 wherein the lower aliphatic alcohol is a straight or branched chain alcohol of 1-4 carbon atoms.

9. A method according to claim 8 wherein the alcohol is methyl alcohol or ethyl alcohol.

10. A method according to claim 1 wherein the solvent is removed from the solution by spray drying.

11. A method according to claim 1 wherein the solvent is removed from the solution by lyophilization.

* * * * *